(12) United States Patent
Norimoto

(10) Patent No.: US 10,603,225 B2
(45) Date of Patent: Mar. 31, 2020

(54) ABSORBENT ARTICLE

(71) Applicant: DAIO PAPER CORPORATION, Ehime (JP)

(72) Inventor: Yoshimi Norimoto, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 387 days.

(21) Appl. No.: 15/512,864

(22) PCT Filed: Sep. 25, 2015

(86) PCT No.: PCT/JP2015/077100
§ 371 (c)(1),
(2) Date: Mar. 21, 2017

(87) PCT Pub. No.: WO2016/052330
PCT Pub. Date: Apr. 7, 2016

(65) Prior Publication Data
US 2017/0290714 A1  Oct. 12, 2017

(30) Foreign Application Priority Data

Sep. 30, 2014 (JP) ................................ 2014-200217

(51) Int. Cl.
*A61F 13/475* (2006.01)
*A61F 13/472* (2006.01)
(Continued)

(52) U.S. Cl.
CPC ........ *A61F 13/47263* (2013.01); *A61F 13/15* (2013.01); *A61F 13/472* (2013.01);
(Continued)

(58) Field of Classification Search
CPC ................ A61F 13/475; A61F 13/4751; A61F 13/4752; A61F 13/4753; A61F 13/49413;
(Continued)

(56) References Cited

U.S. PATENT DOCUMENTS 7,462,174 B2 * 12/2008 Nishitani ............ A61F 13/4753
604/385.04
7,641,642 B2 * 1/2010 Murai ................. A61F 13/4753
604/385.24
(Continued)

FOREIGN PATENT DOCUMENTS

JP  2000-135241  5/2000
JP  2009-118928  6/2009
(Continued)

OTHER PUBLICATIONS

International Search Report dated Dec. 22, 2015 in International (PCT) Application No. PCT/JP2015/077100.

*Primary Examiner* — Catharine L Anderson
(74) *Attorney, Agent, or Firm* — Wenderoth, Lind & Ponack, LLP

(57) ABSTRACT

Absorbent articles including sanitary napkins, panty liners and incontinence pads, wherein an end portion in the longitudinal direction of the absorbent article is reduced from rising by the contraction force of an elastic stretchable member, and the absorption performance is improved and lateral leakage is prevented. In FIG. 5, a sanitary napkin 1 includes a side nonwoven fabric 7 that has an absorber 4 interposed between a permeable front sheet 3 and an impermeable back sheet 2 and forms a solid gather BS rising on each of both side portions on a skin side by a contraction force due to an elastic stretchable member 14. The side nonwoven fabric 7 has a fixed zone 20 joined to the absorbent article 4 side by folding back in both end portions in the longitudinal direction of the napkin, a standing zone 21 rising on a skin side by joining the elastic stretchable member 14 in an intermediate portion in the longitudinal direction of the napkin, and a non-fixed zone 22 where the elastic stretchable member 14 is neither joined between the fixed zone 20 and standing zone 21 nor joined to the absorber 4 side.

5 Claims, 9 Drawing Sheets

(51) Int. Cl.
    *A61F 13/15*     (2006.01)
    *A61F 13/494*     (2006.01)
    *A61F 13/47*     (2006.01)

(52) U.S. Cl.
    CPC ...... *A61F 13/4752* (2013.01); *A61F 13/4758* (2013.01); *A61F 13/49413* (2013.01); *A61F 13/4753* (2013.01); *A61F 13/4942* (2013.01); *A61F 2013/4708* (2013.01)

(58) Field of Classification Search
    CPC ............ A61F 13/4942; A61F 13/49426; A61F 2013/49092
    See application file for complete search history.

(56) References Cited

U.S. PATENT DOCUMENTS

| | | | | |
|---|---|---|---|---|
| 7,708,725 | B2 * | 5/2010 | Tamagawa | .......... A61F 13/4704 604/380 |
| 2011/0046596 | A1 * | 2/2011 | Kudo | .................... A61F 13/474 604/385.24 |

FOREIGN PATENT DOCUMENTS

| | | |
|---|---|---|
| JP | 2010-246614 | 11/2010 |
| JP | 2011-87627 | 5/2011 |
| JP | 2013-27598 | 2/2013 |
| JP | 5475323 | 4/2014 |

* cited by examiner

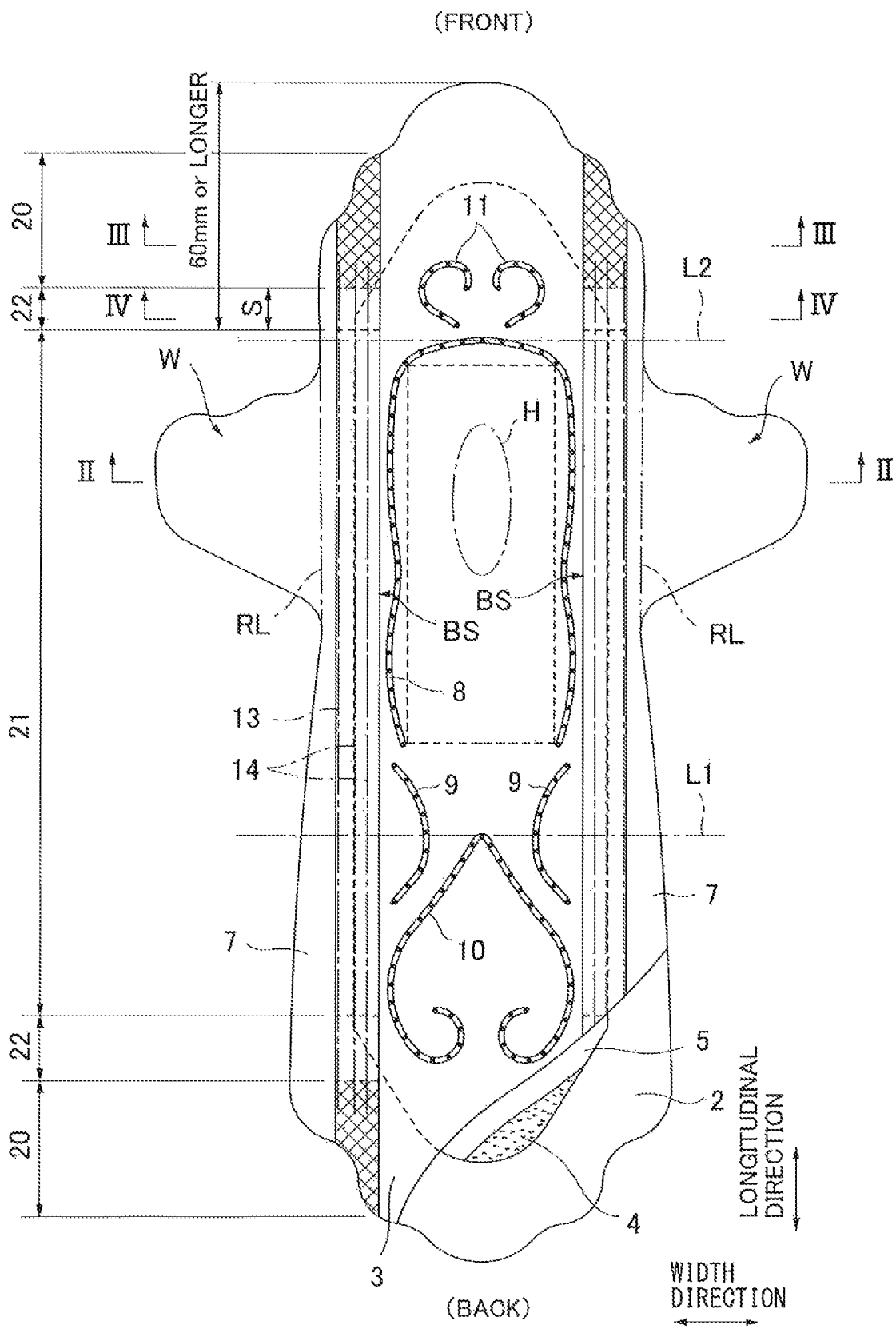
[Fig. 1]

[Fig. 2]
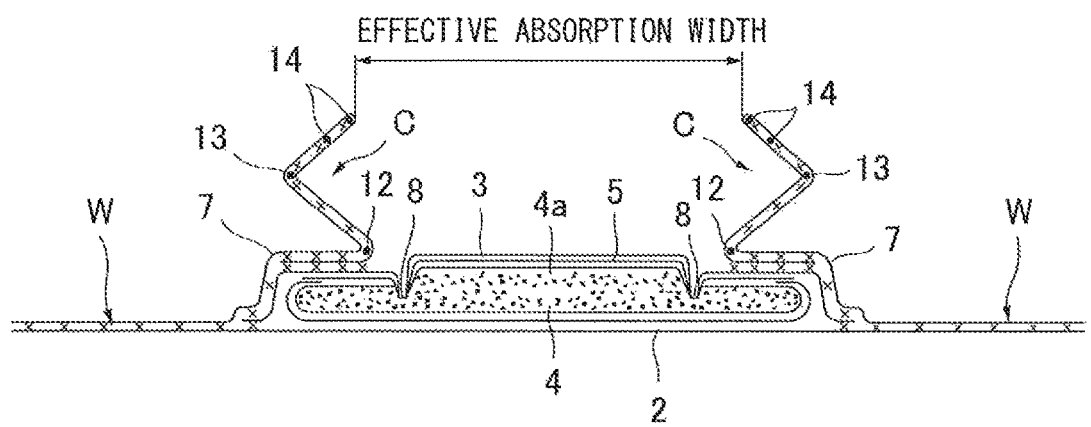
(Fig. 3)
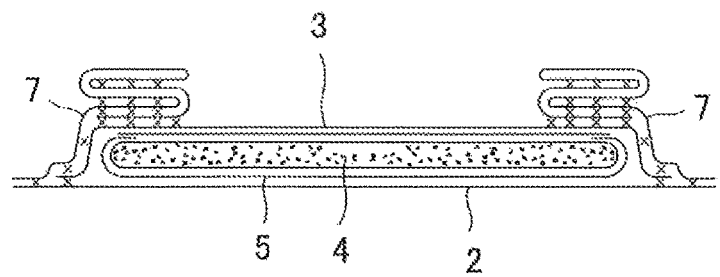

[Fig. 4]
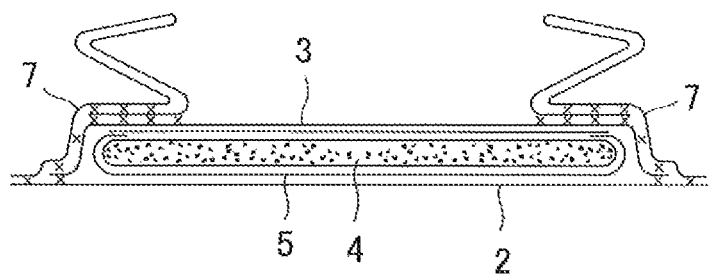

[Fig. 5]
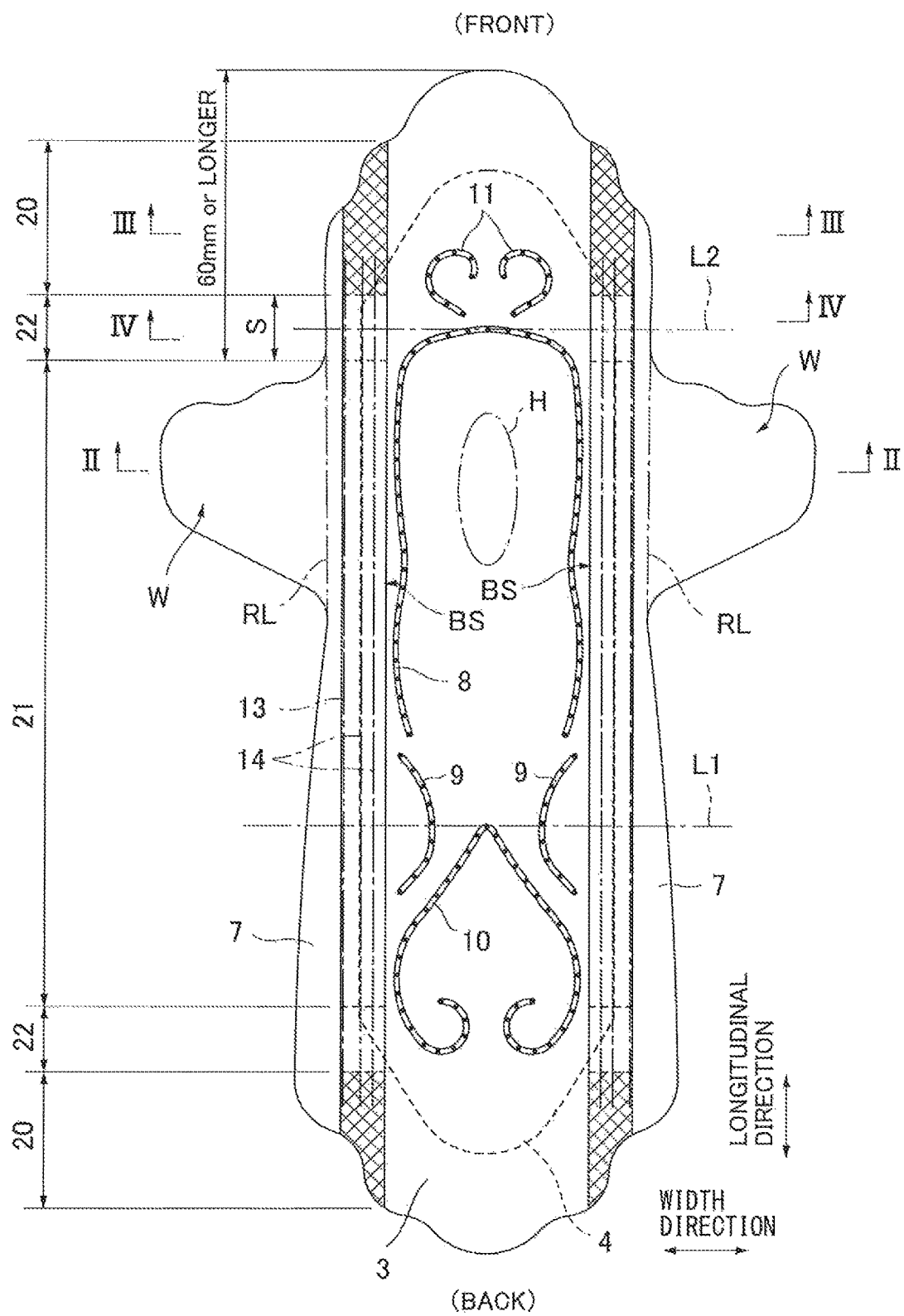

[Fig. 6]
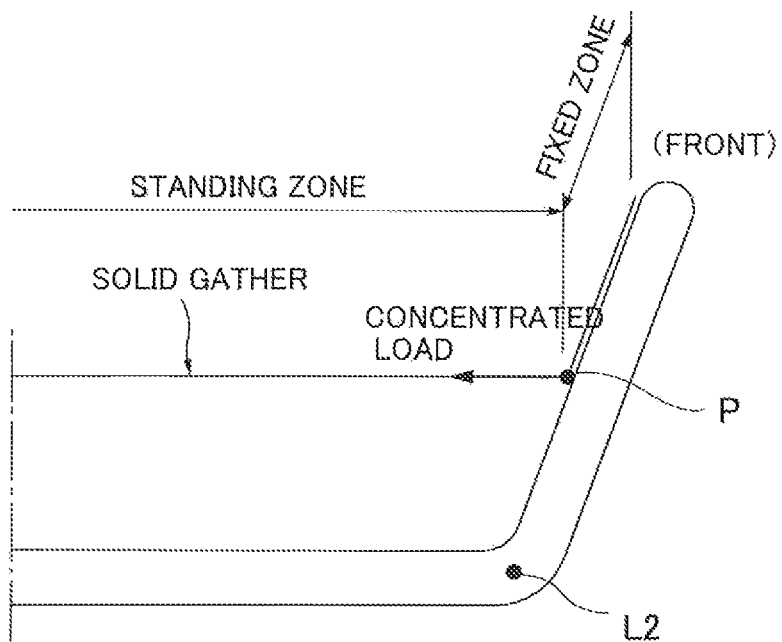
[Fig. 7]
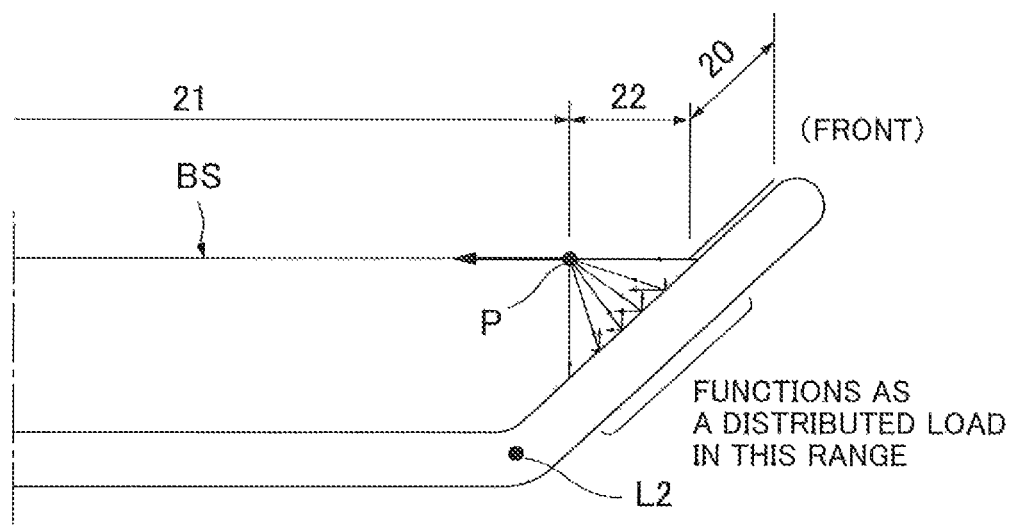

[Fig. 8]
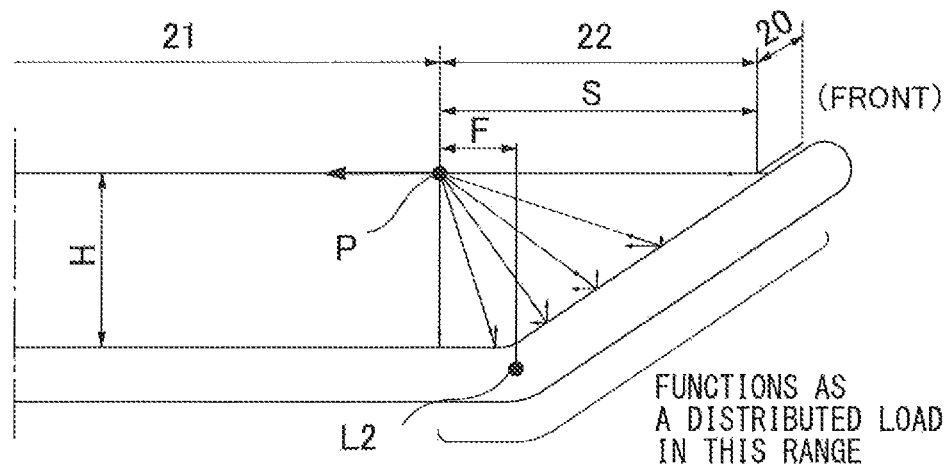

[Fig. 9]
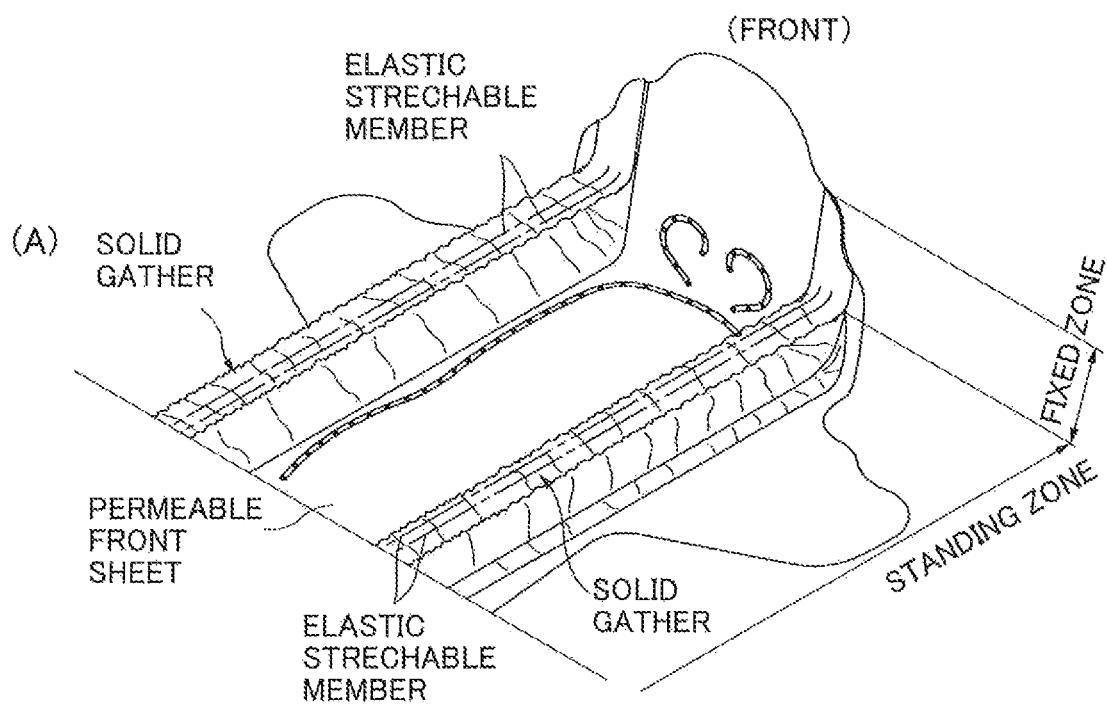
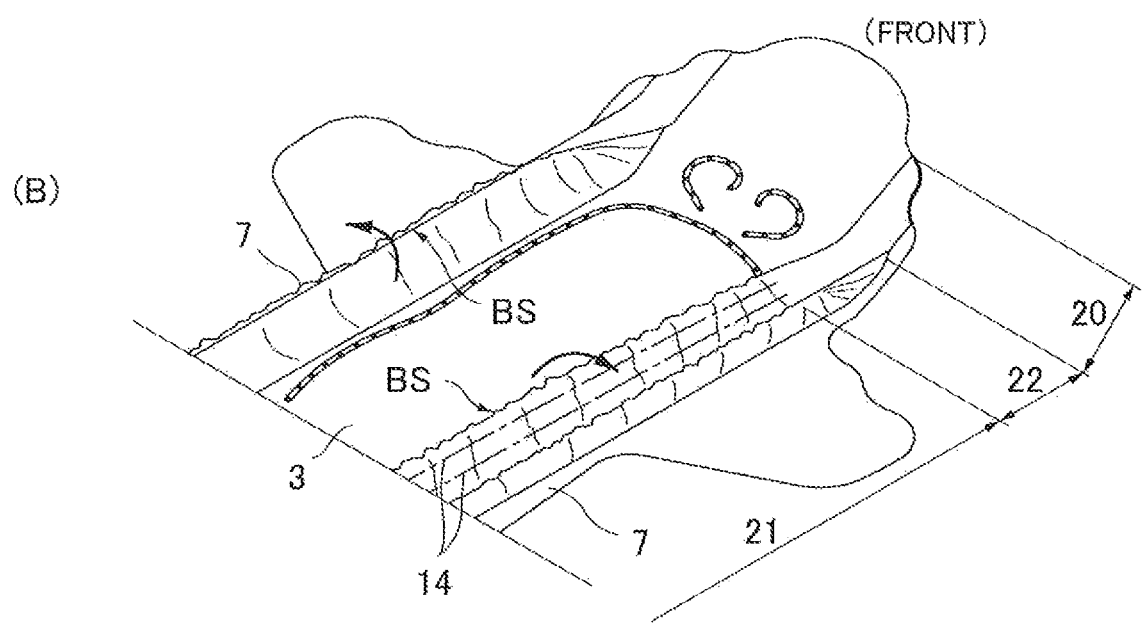

[Fig. 10]
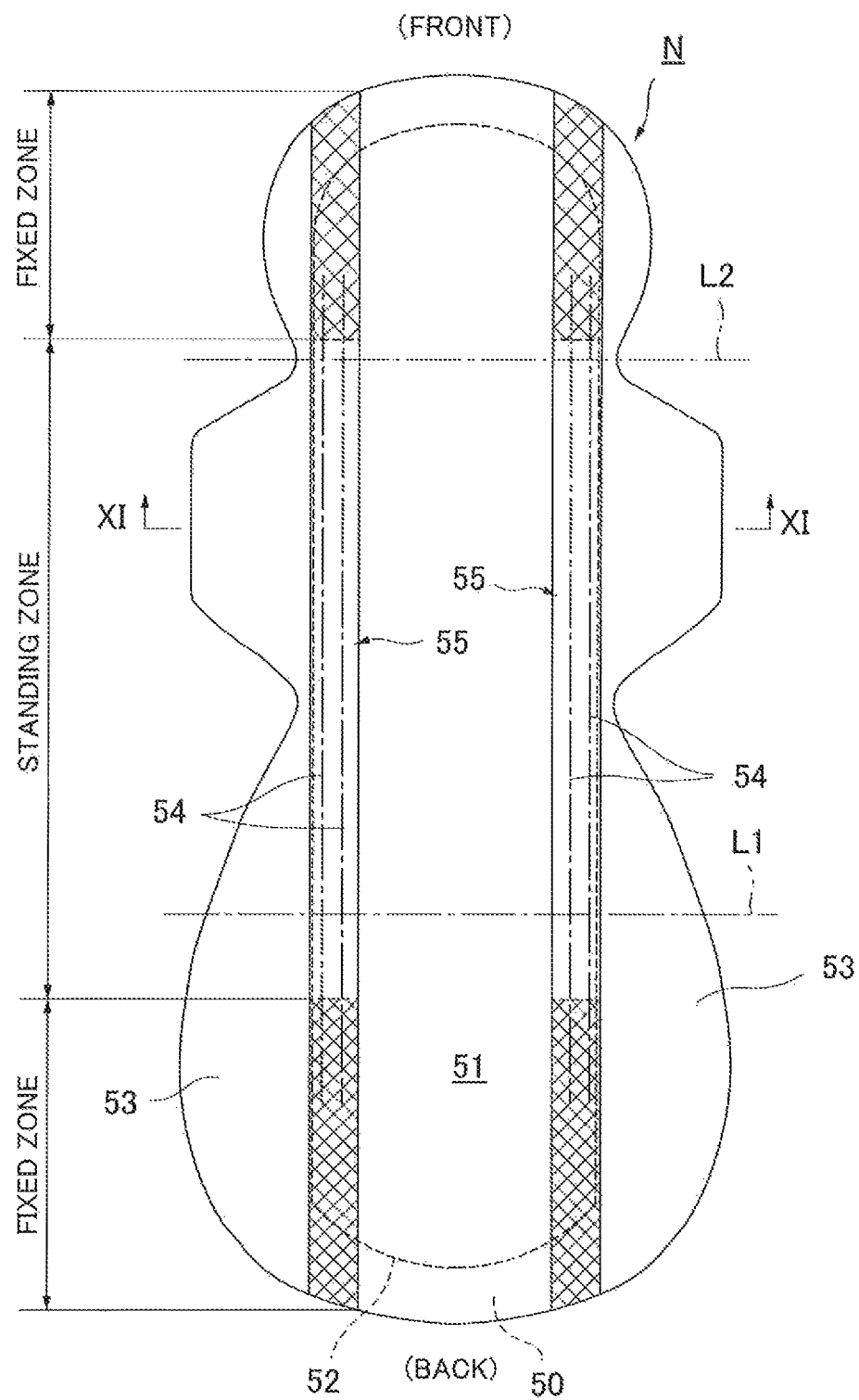

[Fig. 11]
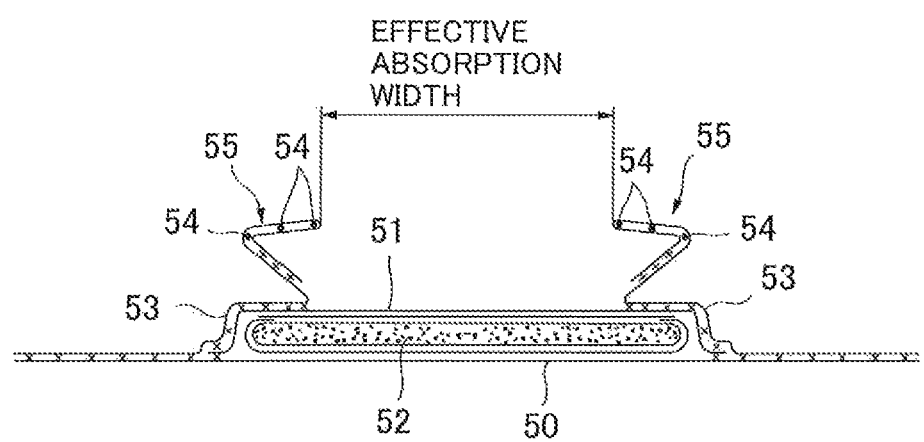

ABSORBENT ARTICLE

TECHNICAL FIELD

The present invention relates to an absorbent articles such as a sanitary napkin, a panty liner, and an incontinence pad for absorbing menstrual blood, vaginal discharge or the like, in particular, relates to an absorbent article provided with a solid gather that rises on a skin side by a contraction force due to an elastic stretchable member on each of both side parts on a skin side.

BACKGROUND ART

So far, as an absorbent article N such as a sanitary napkin, a panty liner, a vaginal discharge sheet or an incontinence pad, as shown in, for example, FIG. 10 and FIG. 11, an article is known, in which, between an impermeable back sheet 50 made of a polyethylene sheet, a polyethylene laminate nonwoven fabric or the like and a permeable front sheet 51 made of a nonwoven fabric, a permeable plastic sheet or the like, an absorber 52 made of cotton pulp or the like is interposed, and, side nonwoven fabrics 53 and 53 is disposed on each of both side parts on a skin side, inside of the side nonwoven fabric 53, an elastic stretchable member 54 made of one or a plurality of thread rubbers is disposed in a stretched state, thus solid gathers 55, 55 that rise on a skin side by the contraction force of the elastic stretchable member 54 are formed. In FIG. 10, L1 and L2 show positions of folding lines that fold the absorbent article N in a longitudinal direction when individually packing the absorbent article N.

The solid gather 55 rises on a skin side by a contraction force due to the elastic stretchable member 54 over a predetermined zone in a longitudinal direction corresponding to at least a body liquid discharge portion H and prevents lateral leakage by damming the body fluid by adhering an apex of the solid gather 55 to a body.

As an absorbent article provided with such solid gathers, in the following Patent Literature 1, an absorbent article is disclosed, in which an elastic body that is disposed in a leakage prevention portion along a longitudinal direction of the absorbent article includes, in the predetermined range containing at least a boundary between a center region and an end part region in the longitudinal direction of the leakage prevention portion, a fixed portion fixed to a sheet in an extended state in the longitudinal direction and a free end that is located outside than the fixed portion in a longitudinal direction and is not fixed to a sheet, wherein the end portion region includes a joining treatment portion in which the sheet joins portions that face with each other and a non-joining treatment portion to which the joining treatment is not applied, wherein the free end is disposed to the non-joining treatment portion.

Further, in the following Patent Literature 2, an absorbent article that has a joined region in which an elastic stretchable member is joined to a body in anteroposterior both end portions in the longitudinal direction of the solid gather, and has a non-joined region in which the elastic stretchable member is not joined to the body in an internal portion in the longitudinal direction of the solid gather sandwiched between these anteroposterior both end portions is disclosed.

PRIOR ART LITERATURES

Patent Literature 1: JP 5475323
Patent Literature 2: JP 2009-118928

SUMMARY OF THE INVENTION

Problem to be Solved by the Invention

However, in a conventional absorbent article, as shown in FIG. 10, since an immediately outside of a standing zone risen on a skin side by a contraction force due to an elastic stretchable member 54 is a fixed zone in which a side nonwoven fabric 53 is folded and fixed to an absorber side together with the elastic stretchable member 54, a contraction force of the elastic stretchable member 54 acted directly as a concentrated load on a portion where the contraction force of the elastic stretchable member 54 of a boundary portion of the fixed zone and the standing zone starts to operate and made an end portion in the longitudinal direction of the absorbent article easy to rise on the skin side (see FIG. 6). There was a case in which since the end portion in the longitudinal direction of the absorbent article rises up greatly on the skin side, when wearing, the end portion in the longitudinal direction of the absorbent article tends to bend and generate twist and unpleasant sensation, and the twist influences on the standing portion of the solid gather, and thereby the leakage prevention effect cannot be sufficiently exhibited. This is the same also for the absorbent article described in the Patent Literature 2.

On the other hand, in the absorbent article described in the Patent Literature 1, an elastic body is fixed to a sheet at a fixed portion disposed on a boundary between a center region and an end part region, and, outside than the fixed portion in the longitudinal direction, a free end in which the elastic body is not fixed to the sheet is formed. However, since on an immediately outside of the fixed portion, a joining treatment portion in which sheets are joined with each other is formed, a structure that can sufficiently suppress the rising of the end portion in the longitudinal direction of the absorbent article was not formed.

Further, as shown in FIG. 10, in a conventional absorbent article, continuously from an immediately outside a of standing zone where the side nonwoven fabric 53 rises on a skin side by the contraction force due to the elastic stretchable member 54, a fixed zone in which the side nonwoven fabric 53 is folded back and integrally joined on the absorbent article side together with the elastic stretchable member 54 is disposed. Therefore, a skin contact surface of the standing zone rises on a skin side in a state folded in the fixed zone, that is, as in the state where the skin contact surface collapsed inward (see FIG. 9(A)). That is, since a separation width of apexes of left and right solid gathers becomes a width that is hardly different from a separation width folded back in the fixed zone, an effective absorption width that is the separation width between the apexes of the left and right solid gathers is narrow, and an absorption performance and a lateral leakage prevention effect were lowered.

In this connection, a main problem of the present invention is to provide, in an absorbent article provided with solid gathers that rise respectively on a skin side in both side portions on a skin side, an absorbent article in which an end portion in the longitudinal direction of the absorbent article is reduced from rising by the contraction force of an elastic stretchable member, and the absorption performance and lateral leakage prevention effect are improved.

Means for Solving the Problem

As a present invention according to embodiment 1 for solving the above-described problems, an absorbent article is provided, which includes a side nonwoven fabric that has an absorber interposed between a permeable front sheet and a back sheet and forms a solid gather that rises on a skin side by a contraction force due to an elastic stretchable member at each of both side portions on a skin side, wherein the side nonwoven fabric has a fixed zone joined to the absorber article side by folding back in both end portions in the longitudinal direction of the absorbent article, a standing zone rising on a skin side by joining the elastic stretchable member in an intermediate portion in the longitudinal direction of the absorbent article, and a non-fixed zone where the elastic stretchable member is neither joined between the fixed zone and standing zone nor joined to the absorbent article side.

According to the invention described in embodiment 1, the side nonwoven fabric disposed to each of both side portions on a skin side has a fixed zone joined to the absorbent article side by folding back in both end portions in the longitudinal direction of the absorbent article, a standing zone rising on a skin side by joining the elastic stretchable member in an intermediate portion in the longitudinal direction of the absorbent article, and a non-fixed zone where the elastic stretchable member is neither joined between the fixed zone and standing zone nor joined to the absorbent article side. Thus, in the present absorbent article, since the non-fixed zone is disposed between the fixed zone and the standing zone, a fixed end of the elastic stretchable member joined to the standing zone is not directly fixed to the fixed zone but becomes a movable point where the non-fixed zone is interposed in a space with the fixed zone, a tensile force acting on the end portion of the elastic stretchable member becomes smaller. Further, since the contraction force of the elastic stretchable member acts not as a concentrated load but as a distributed load via the side nonwoven fabric of the non-fixed zones, an angle by which the end portion of the absorbent article rises on the skin side can be suppressed smaller.

Further, since the fixed end of the elastic stretchable member fixed to the standing zone becomes the movable point, compared with a conventional one in which the elastic stretchable member is joined together with the side nonwoven fabric to the fixed zones, the solid gather itself can be freely deformed by the contraction force of the elastic stretchable member and the apex of the solid gather rises greatly on the skin side. Therefore, since an effective absorption width that is the separation width between the apexes of left and right solid gathers is enlarged to be able to receive the body fluid in a wider range, an absorption performance is improved and, at the same time, a damming effect of the body fluid by the solid gathers is improved, and the lateral leakage prevention effect can be improved.

As an invention according to embodiment 2, the absorbent article according to embodiment 1 in which the non-fixed zone is formed with a length of 10 mm or longer in the longitudinal direction of the absorbent article is provided.

In the invention described in embodiment 2, when the non-fixed zone is formed with a length of 10 mm or longer in the longitudinal direction of the absorbent article, the fixed end of the elastic stretchable member of the standing zones surely works as the movable point. Therefore, the solid gather that rises on the skin side by the contraction force due to the elastic stretchable member is formed in the standing zone without being affected substantially by fixing the side nonwoven fabric in the fixed zones.

As an invention according to embodiment 3, the absorbent article according to any one of embodiments 1 and 2 in which a front side end portion of the standing zone is disposed at a position 60 mm or more distanced from a front end of the absorbent article is provided.

According to the invention described in embodiment 3, by disposing a front side end portion of the standing zone at a position 60 mm or more distanced from a front end of the absorbent article, an operating point of the contraction force due to the elastic stretchable member becomes a position sufficiently distanced from the front end of the absorbent article. Therefore, the rising of the front side portion of the absorbent article can be more surely made smaller.

As an invention according to embodiment 4, the absorbent article according to anyone of embodiments 1 to 3 in which the front side end portion of the standing zone is disposed backward than a folding line that folds the front side portion of the absorbent article when the absorbent article is individually packed is provided.

In the invention described in embodiment 4, a relative positional relationship between the front side end portion of the standing zone and a folding line along which the front side end portion of the absorbent article is folded when individually packing the absorbent article is defined. While the front side end portion of the standing zone may be disposed on a front side than the folding line along which the front side portion of the absorbent article is folded back when individually packing the absorbent article, it is preferable to dispose backward than the folding line from the viewpoint that a rotation moment for rising the front side portion of the absorbent article can be minimized.

As an invention according to embodiment 5, the absorbent article described in any one of embodiments 1 to 4 in which in a width direction range of at least the solid gather, a contour line of an end portion in the longitudinal direction is unevenly formed is provided.

In the invention described in embodiment 5, when the contour line of an end portion in the longitudinal direction is unevenly formed in a width direction range of at least solid gather, the end portion can be prevented from bending or twisting and can be deformed along a curved line of a body, thus unpleasant feeling can be reduced. The contour line of the end portion in the longitudinal direction is both or any one of a contour line on the front side in the longitudinal direction and a contour line on a back side in the longitudinal direction.

As an invention according to embodiment 6, the absorbent article described in any one of embodiments 1 to 5 in which the elastic stretchable member is distributed eccentrically much on a width direction inside of the absorbent article in a width direction range of the solid gathers is provided.

In the invention described in embodiment 6, when the elastic stretchable member is distributed eccentrically much on the width direction inside of the absorbent article in the width direction range of the solid gather, the deformation in the width direction in which a width direction outside of the solid gather curves inward by the contraction force of the elastic stretchable member can be suppressed.

Effect of the Invention

As detailed in the above, according to the present invention, the end portion in the longitudinal direction of the absorbent article can be reduced from rising by the contraction force of the elastic stretchable member, and the absorption performance and the lateral leakage prevention effect can be improved.

BRIEF DESCRIPTION OF THE DRAWINGS

FIG. 1 is a partially broken development view of a sanitary napkin 1 according to a first embodiment of the present invention.

FIG. 2 is an arrow view taken along a II-II line of FIG. 1.

FIG. 3 is an arrow view taken along a line of FIG. 1.

FIG. 4 is an arrow view taken along a IV-IV line of FIG. 1.

FIG. 5 is a development view of the sanitary napkin 1 according to a second embodiment.

FIG. 6 is a cross-sectional view in the longitudinal direction showing a modified state of a conventional absorbent article.

FIG. 7 is a cross-sectional view in the longitudinal direction showing a modified state of the sanitary napkin 1 according to a first embodiment.

FIG. 8 is a cross-sectional view in the longitudinal direction showing a modified state of the sanitary napkin 1 according to a second embodiment.

FIG. 9 is a perspective view in which (A) shows a conventional absorbent article, and (B) shows a modified state of the present sanitary napkin.

FIG. 10 is a development view showing a conventional absorbent article N.

FIG. 11 is an arrow view taken along a XI-XI line of FIG. 10.

MODES FOR CARRYING OUT THE INVENTION

In what follows, embodiments of the present invention will be described in detail with reference to the drawings.

(Example of Structure of Sanitary Napkin 1)

A sanitary napkin 1 according to the present invention includes, as shown in FIGS. 1 to 4, an impermeable back sheet 2 made of a polyethylene sheet, a polypropylene sheet or the like, a permeable front sheet 3 that smoothly transmits menstrual blood, a vaginal discharge or the like, an absorber 4 made of cotton pulp, synthetic pulp or the like interposed between these both sheets 2 and 3, a crepe paper 5 surrounding the absorber 4 for improving shape retention and diffusibility of the absorber 4, and side nonwoven fabrics 7 and 7 that form a pair of solid gathers BS and BS disposed by protruding on a skin side in a predetermined zone in the longitudinal direction with a substantial side edge portion of the absorber 4 as a rising base end and so as to contain at least body fluid discharge portion H. In the surrounding of the absorber 4, in upper and lower edge portions thereof, an outer edge portion of the impermeable back sheet 2 and permeable front sheet 3 is joined by an adhesive such as hot melt or by adhesion means such as heat seal or the like, further, in both side end portions thereof, the impermeable back sheet 2 extending laterally than the absorber 4 and the side nonwoven fabric 7 are joined by an adhesive such as a hot melt or by the adhesion means such as a heat seal or the like.

In what follows, further a structure of the sanitary napkin 1 will be described in more detail.

In the impermeable back sheet 2, a sheet material having at least impermeability such as an olefinic resin sheet such as polyethylene or polypropylene can be used. However, other than these, a laminate nonwoven fabric obtained by laminating a nonwoven fabric on the polyethylene sheet or the like, further, a nonwoven fabric sheet or the like can be used after substantially securing the impermeability by interposing a waterproof film (in this case, the waterproof film and the nonwoven fabric constitute an impermeable back sheet). In recent years, from the viewpoint of a stuffiness prevention property, a moisture permeable one tends to be used. This waterproof and moisture permeable sheet material is a microporous sheet obtained by monoaxially or biaxially stretching after molding a sheet by melting and kneading an inorganic filler in an olefinic resin such as polyethylene or polypropylene.

As the permeable front sheet 3, a porous or nonporous nonwoven fabric or a porous plastic sheet is preferably used. As a raw material fiber that constitutes the nonwoven fabric, other than synthetic fibers, for example such as olefin system such as polyethylene, polypropylene or the like, polyester system, polyamide system, or the like, recycled fiber such as rayon, cupra, or the like, and natural fiber such as cotton or the like may be used, and the nonwoven fabric obtained according to an appropriate processing method such as a span race method, a span bond method, a thermal bond method, a melt-blown method, a needle punch method or the like may be used. Among these processing methods, the span race method is excellent in having rich flexibility and drape property, and the thermal bond method is excellent in having high bulkiness and compression restorability.

The absorber 4 interposed between the impermeable back sheet 2 and the permeable front sheet 3 is formed of, for example, a cotton-like pulp and a water absorption polymer. The water absorption polymer is mixed, for example, as a granular powder in the pulp that constitutes the absorber. As the pulp, what are made of cellulose fibers such as chemical pulp, molten pulp or the like obtained from wood, or artificial cellulose fibers such as rayon, acetate or the like are used, and softwood pulp having a longer fiber length than hardwood pulp is preferably used from the viewpoint of function and cost. Like the present example, when a crepe paper 5 that surrounds the absorber 4 is disposed, resultantly, the crepe paper 5 is interposed between the permeable front sheet 3 and absorber 4, thus, the body fluid is speedily diffused by the crepe paper 5 excellent in the absorption performance and the menstrual blood or the like can be prevented from turning back.

Further, the absorber 4 may be mixed with the synthetic fibers. As the synthetic fibers, for example, polyolefin system such as polyethylene, polypropylene, or the like, polyester system such as polyethylene terephthalate, polybutylene terephthalate, or the like, polyamide system such as nylon, or the like, and copolymers thereof may be used, and two kinds thereof may be mixed and used. Further, also a sheath/core fiber with a high-melting point fiber as a core and a low-melting point fiber as a sheath, a side-by-side fiber, and a composite fiber such as divided fiber may be used. The synthetic fiber is desirable to be used after a surface treatment is applied with a hydrophilizing agent, in the case of a hydrophobic fiber, so as to impart affinity to the body fluid.

As shown in FIG. 1, it is desirable to prevent the lateral leakage by imparting various embossments from an outer surface side of the permeable surface sheet 3 to promote retention and improve the absorption performance of the body fluid. In the present sanitary napkin 1, the embossment is constituted of, as shown in FIG. 1, a first embossment 8 that has a center-high portion 4a of the absorber high on the skin side in a center part in a width direction and is formed in a substantially reversed C character shape in a plan view having an opened back side so as to surround both sides and a front side of the center-high portion 4a, second embossments 9 and 9 that are formed by distancing on both sides with an interval opened on the back side of the first embossment 8 and by arcs each having a center of curvature on the outside of the napkin 1, a third embossment 10 that is midway of the second embossments 9 and 9 on both sides and formed in substantially reversed V character shape in which separation width expands toward back side from the center portion in the napkin width direction, and a fourth embossment 11 formed in a substantially heart shape in a plan view, which separates to both sides in the width direction with a space opened on a front side of the first embossment 8.

On the other hand, each of both side portions of a front side of the present sanitary napkin 1 is provided with side nonwoven fabrics 7 and 7 over almost all length of the napkin 1 along a longitudinal direction, a part of the side nonwoven fabrics 7 and 7 is extended on the lateral side and forms wing-like flaps W and W together with a part of the impermeable back sheet 2 extended similarly to the lateral side. On an outside surface side of the impermeable back sheet 2 of the wing-like flaps W and W, a wing slippage prevention adhesive layer (not shown in the drawing) is provided, and, at the time of wearing a short, the wing-like flaps W and W are folded back onto a reverse side at a position of a folding line RL to fasten by winding on a crotch portion of the short. Similarly, on an outer surface side of the impermeable back sheet 2 of a body portion in which the absorber 4 is interposed, a body slippage prevention adhesive layer (not shown in the drawing) is provided.

As the side nonwoven fabric 7, from the viewpoint of important functions, a water-repellent treated nonwoven fabric or a hydrophilized nonwoven fabric can be used. For example, when a function of, such as, preventing the menstrual blood, virginal discharge or the like or of enhancing a skin contact feeling is considered important, it is desirable to use a water-repellent treated nonwoven fabric on which a silicone-base, paraffin-base, or alkyl chromic chloride-base water-repelling agent or the like is coated. Further, when the absorption performance of the menstrual blood or the like in the wing-like flaps W and W is considered important, after making the synthetic fiber swellable or porous by a method of polymerizing by co-existing a compound having a hydrophilic group, for example, an oxidation product of polyethylene glycol in a manufacturing process of the synthetic fiber, or a method of precipitating metal hydroxide by treating a synthetic fiber with a metal salt such as stannic chloride to partially dissolve to make a surface porous, the hydrophilicity is imparted by applying a capillary action, and a hydrophilized nonwoven fabric provided is used.

As shown in FIG. 2, an internal side portion of the side nonwoven fabric 7 is folded back into substantially double, and appropriate elastic stretchable members 12 to 14 are disposed inside of the double sheet. Specifically, at a base end portion in the height direction of the inside of the double sheet, an elastic stretchable member 12 of which both ends or an appropriate position in the longitudinal direction is fixed is disposed, and an elastic stretchable member 13 in which in an intermediate portion in its height direction, both ends or an appropriate position in the longitudinal direction is fixed is disposed, and at an upper side site of the elastic stretchable member 13, one or a plurality of, in the illustrated example, two elastic stretchable members 14 and 14 are disposed in a state in which both ends or an appropriate position in the longitudinal direction is fixed. The double sheet portion is, in the anteroposterior end portion of the sanitary napkin 1, as shown in FIG. 3, by adhering to the absorber 4 side in a laminated state by folding in a reversed Z character shape in cross section, with a disposition site of the elastic stretchable member 13 a bending point, solid gathers BS and BS forming an inverted V character shape in cross section are formed. The side nonwoven fabric 7 will be described in more detail in a later part.

As the elastic stretchable members 12 to 14, a thread-like one that uses a raw material such as rubber or silicone used usually is preferred. A diameter of the rubber thread is preferably 300 to 1000 dtex and more preferably 400 dtex to 550 dtex.

As an expansion rate of the elastic stretchable members 12 to 14 is set to 105% to 160%, and preferably set to 120% to 140% with a natural length as 100%. The elastic stretchable members 12, 13 and 14 are preferably disposed at the same expansion rate.

The sanitary napkin 1 is individually packed by appropriately folding in the longitudinal direction. Specifically, after folding back the wing-like flaps W and W onto the permeable front sheet 3 side at the folding lines RL and RL of the base end portion, the sanitary napkin 1 is individually packaged with an individual packing sheet (not shown in the drawing). In an individual packing method, as shown in FIG. 1, after folding back a napkin back side portion together with the individual packing sheet onto the permeable front sheet 3 side at a folding line L1 position on the back side, the napkin front side portion is folded into three together with the individual packing sheet on the permeable front sheet 3 side at a front side folding line L2 position, and, by sealing each of opened end portions of the individual packing sheet, a packed state is obtained. A folding number of the sanitary napkin 1 may be set to 4 or more.

A front side folding line L2 is, as shown in FIG. 1, preferably disposed at a position that passes through a front side end portion of the first embossment 8 which is formed into a substantially reversed C character shape in a plan view. Thus, with an embossed portion extending in the napkin width direction on a front side of the first embossment 8 as a flexible shaft, the napkin front side portion tends to be readily folded. Further, a back side folding line L1 is preferably disposed at a position that passes a front side end portion of the third embossment 10 formed into a substantially reversed V character shape. Thus, with a napkin width direction line that passes a substantially reversed V character shape base end portion of a width direction center portion of the third embossment 10 as a flexible shaft, the napkin back side portion tends to be readily folded back.

(Side Nonwoven Fabric 7)

Each of the side nonwoven fabric 7 is, as shown in FIG. 1, partitioned into predetermined zones in the napkin longitudinal direction depending on a form of a doubly folded internal side portion. The zone is constituted of fixed zones 20 and 20 joined on the absorber 4 side by folding the internal side portion in the both end portions in the longitudinal direction of the sanitary napkin 1, a standing zone 21 in which each of the elastic stretchable members 12 to 14 is joined to the side nonwoven fabric 7 to form a solid gather BS rising on the skin side by the contraction force due to the elastic stretchable member in an intermediate portion in the longitudinal direction of the sanitary napkin 1, and non-fixed zones 22 and 22 in which neither the elastic stretchable members 12 to 14 are joined to the side nonwoven fabric 7 nor the side nonwoven fabric 7 is joined to the absorber 4 side between the fixed zone 20 and standing zone 21. In FIG. 1 and FIG. 5 that will be described below, while each of the elastic stretchable members 12 to 14 is shown by extending to a midway of the non-fixed zone 22 and the fixed zone 20 exceeding the standing zone 21, the elastic stretchable members 12 to 14 of the non-fixed zone 22 and the fixed zone 20 extend in a natural state in which the contraction force due to the elastic stretchable members 12 to 14 does not act. Further, a range extending in a natural state while exceeding the standing zone 21 is optional. For example, like an illustrated example, the range may exceed the non-fixed zone 22 to extend to a middle of the fixed zone 20, may be up to a middle of the non-fixed zone 22, or may not be extended.

The fixed zone 20, standing zone 21 and non-fixed zone 22 are continuously disposed in the napkin longitudinal direction without disposing a space therebetween, and are disposed over an entire length in the longitudinal direction of the napkin of the side nonwoven fabric 7.

The fixed zone 20 is a zone in which, as shown in FIG. 3, the internal side portion of a doubly folded side nonwoven fabric 7 is folded into a Z character shape in cross section view, and mutually facing sheets are joined by joining means such as a hot-melt adhesive or a heat seal. In this fixed zone 20, since the elastic stretchable members 12 to 14 are not joined in a stretched state inside of the double sheet, the contraction force due to the elastic stretchable membranes 12 to 14 does not act. The inside of the double sheet may be joined or may not be joined.

The standing zone 21 is, as shown in FIG. 1, disposed in a range in the longitudinal direction containing at least a body fluid discharge portion H. In an example shown in FIG. 1, the standing zone 21 is continuously disposed from a front side base end portion of the wing-like flap W to a predetermined position behind the sanitary napkin. In the standing zone 21, as shown in FIG. 2, by disposing the elastic stretchable members 12 to 14 joined to the side nonwoven fabric 7 by the joining means such as a hot-melt adhesive at least both ends of the standing zone 21, preferably at both ends and at an appropriate position in the longitudinal direction of the standing zone 21, to the inside of the double sheet, with the disposition site of the elastic stretchable member 13 as a bending point, the solid gathers BS and BS rising on a skin side are formed while forming pockets C and C that direct an opening to the inside in inverted V character shape in cross section view. In the standing zone 21, in a state where a doubly folded side nonwoven fabric 7 is folded, the mutually facing sheets are not joined, and, in a use state, as shown in FIG. 2, the doubly folded side nonwoven fabric 7 rises on a skin side by the contraction force due to the elastic stretchable member. The inside of the double sheet is joined only by a joining site of the elastic stretchable members 12 to 14 and the side nonwoven fabric 7, the sites other than this may not be joined, or sites other than the joining sites of the elastic stretchable member may be joined.

In the non-fixed zone 22, as shown in FIG. 4, the elastic stretchable members 12 to 14 are not joined in a stretched state inside of the double sheet, thus the contraction force due to the elastic stretchable members 12 to 14 does not act. Further, in the non-fixed zone 22, without being joined between mutually facing sheets in a state where the doubly folded nonwoven side fabric 7 is folded, in a use state, as shown in FIG. 4, the solid gathers rise on the skin side by being pulled when the standing zone 21 rises on the skin side, and this standing height becomes higher as comes nearer to the standing zone 21.

Then, a relative positional relationship between the respective zones 20 to 22 and the folding line when the sanitary napkin 1 is individually packed. As a first embodiment, as shown in FIG. 1, in a front side of the sanitary napkin 1, a front side end portion of the standing zone 21 is disposed so as to locate on a front side than a folding line L2 that folds a front side portion of the sanitary napkin 1. That is, the folding line L2 that folds the front side portion of the sanitary napkin 1 is disposed at a position that passes the standing zone 21.

Further, as a second embodiment, as shown in FIG. 5, in the front side of the sanitary napkin 1, the front side end portion of the standing zone 21 is disposed so as to locate on a back side than the folding line L2 that folds the front side portion of the sanitary napkin 1. That is, the folding line L2 that folds the front side portion of the sanitary napkin 1 is disposed at a position that passes the non-fixed zone 22.

In the present sanitary napkin 1 formed of the above configuration, since the non-fixed zone 22 is disposed between the fixed zone 20 and the standing zone 21, compared with the conventional one, in a state taken out of an individually packed state, effect that the rising of a napkin end portion can be suppressed smaller, and the absorption performance and the lateral leakage prevention effect are improved can be exhibited. When explained in more detail, in the case of the conventional absorbent article N shown in FIG. 10 and FIG. 11, as shown in FIG. 6, continuously from the immediately outside of the standing zone where a side nonwoven fabric 53 rises on the skin side by the contraction force due to the elastic stretchable member 54 to form a solid gather 55, a fixed zone that fixes the side nonwoven fabric 53 in a folded state on the absorber side is disposed. Thus, a fixed end P of an elastic stretchable member 54 and an inner side position of the fixed zone are formed so as to coincide. As a result, since the contraction force of the elastic stretchable member 54 directly acts as a concentrated load at the fixed end P, a force that raises the edge portion of the absorbent article becomes larger, in a state taken out of the individual package, a front side of the absorbent article rises greatly on the skin side with a front side folding line L2 as a bending shaft.

By contrast, in the sanitary napkin 1 according to the first embodiment where the front side end portion of the standing zone 21 is located on the front side than the folding line L2, as shown in FIG. 7, since the non-fixed zone 22 is provided between the fixed zone 20 and the standing zone 21, the fixed end P of the elastic stretchable member 14 joined to the standing zone 21 is not fixed directly to the fixed zone 20 but becomes a movable point with the non-fixed zone 22 interposed in a space with the fixed zone 20, thus, a tensile force acting on the fixed end P of the elastic stretchable member 14 becomes smaller. Further, since, between the fixed end P of the elastic stretchable member 14 and the fixed zone 20 where the side nonwoven fabric 7 is fixed to the absorber side, the non-fixed zone 22 where neither the side nonwoven fabric 7 is fixed to the absorber side nor the contraction force due to the elastic stretchable member works is disposed, the contraction force acting on the fixed end P of the elastic stretchable member 14 acts as a distributed load via the side nonwoven fabric 7 of the non-fixed zone 22. Therefore, the front side portion of the sanitary napkin 1 can be suppressed from rising.

On the other hand, in the case of the sanitary napkin 1 according to the second embodiment where the front side end portion of the standing zone 21 is located on the back side than the folding line L2, as shown in FIG. 8, similarly as the case of the first embodiment, since the fixed end P of the elastic stretchable member 14 becomes the movable point to the napkin body, the tensile force acting on the fixed end P becomes smaller. Further, since the contraction force of the elastic stretchable member 14 acts as the distributed load via the non-fixed zone 22, the rising of the front side portion of the sanitary napkin 1 can be suppressed smaller.

Further, since the fixed end P of the elastic stretchable member 14 is located on the back side than the folding line L2 that folds the front side portion of the sanitary napkin 1 during individual packing, a rotation moment that makes the front side portion of the sanitary napkin 1 rise can be minimized. If a base point (folding line L2) of bending is located at a center between the fixed end P of the elastic stretchable member 14 and an internal side position of the fixed zone 20 (S/2=F), a rotation moment of an upward component force can be made zero, and the rotation moment due to a horizontal component force can be also made significantly smaller. A dimension of a distance S (a length in the longitudinal direction of the napkin of the non-fixed zone 22) between the fixed end P of the elastic stretchable member 14 and an internal side position of the fixed zone 20 is H/2 or higher, preferably 2H/3 or higher, and more preferably H or higher relative to a rising height H of the solid gather BS.

Further, by disposing the non-fixed zone 22 between the fixed zone 20 and the standing zone 21, as shown in FIG. 9, a rising state of a skin contact surface of the solid gather BS becomes also excellent. That is, in the conventional absorbent article, as shown in FIG. 9(A), continuously from the immediate outside of the standing zone, a fixed zone in which the elastic stretchable member and the side nonwoven fabric are fixed is disposed. Therefore, the skin contact surface of the solid gather (a surface that rises most on the skin side) protrudes on the skin side with the skin contact surface folded in the fixed zone and joined to the absorber side. That is, as shown in FIG. 11, the skin contact surface of the solid gather protrudes to the skin side with a planar state in which the skin contact surface of the solid gather collapsed onto an inner side fixed in the fixed zone substantially retained. Therefore, as shown in FIG. 11, an effective absorption width that is a separation width between apexes of left and right solid gathers is narrow, that is, an effective absorption width that substantially absorbs the body fluid became narrower. By contrast, in the present sanitary napkin 1, as shown in FIG. 9(B), the non-fixed zone 22 where the side nonwoven fabric 7 is not fixed between the standing zone 21 and the fixed zone 20 is provided. Therefore, the deformation due to the elastic stretchable member 14 in the standing zone 21 is performed without being influenced by a state fixed in the fixed zone 20, and the skin contact surface of the solid gather BS deforms so as to expand outward by the contraction force of the elastic stretchable member 14. Thus, as shown in FIG. 2, the effective absorption width that is the separation width between apexes of left and right solid gathers BS and BS becomes wider, that is, the body fluid can be absorbed by a large area.

The length S in the longitudinal direction of the napkin of the non-fixed zone 22 is set to, when shown by a specific length, 10 mm or longer, preferably from 10 mm to 40 mm, and more preferably from 10 mm to 20 mm. When the non-fixed zone 22 is formed with a length more than a predetermined length, since a state where the side nonwoven fabric 7 is folded and fixed in the fixed zone 20 becomes difficult to influence on a state that rises on the skin side in the standing zone 21, the solid gather BS of the standing zone 21 rises more excellently.

As shown in FIG. 1 and FIG. 5, the fixed end P on the front side of the elastic stretchable member 14 is disposed at a position separated from the front end of the sanitary napkin 1 by 60 mm or larger, preferably by from 60 mm to 100 mm, and more preferably by from 60 mm to 70 mm. This distance is a length in a state where the sanitary napkin 1 is developed by stretching the elastic stretchable members 12 to 14 (development state shown in FIG. 1 and FIG. 5). Thus, since an operating point of the contraction force due to the elastic stretchable member 14 operating on the front side portion of the sanitary napkin 1 becomes a position sufficiently separated from the front end, the rising of the front side portion of the sanitary napkin 1 due to the contraction force can be surely made smaller.

A contour line of the sanitary napkin 1, in the range in the width direction within which at least the solid gather BS is formed, the contour line on a front side in the longitudinal direction is preferably formed unevenly. The range in the width direction where the solid gather BS was formed is a range in the width direction of the napkin where the solid gather BS rising on the skin side is formed, and a range in a napkin width direction where, in the fixed zone 20, the side nonwoven fabric 7 is folded and fixed to the absorber 4 side. Further, that a contour line is unevenly formed means that the contour line forms a convex portion protruding outward and a concave portion receding inward respectively at least one to a straight line or a curved line that passes a center portion of the contour line formed in wave. By forming the contour line unevenly in this range, folds or twists of the front side end portion can be prevented from occurring, at the same time, the front side end portion tends to de easily deformed along a body curve, and unpleasant feeling can be reduced. The range within which the contour line of the napkin is unevenly formed can be formed, as shown in FIG. 1 and FIG. 5, up to the range exceeding the range in the width direction of the solid gather BS.

The elastic stretchable member 14 disposed on the skin contact surface of the solid gather BS is preferably present eccentrically much in a napkin width direction inside of the width direction range of the solid gather BS. The width direction range of the solid gather BS is a napkin width direction range in which the side nonwoven fabric 7 is folded and fixed to the absorber 4 side in the fixed zone 20. To be mostly unevenly distributed in the napkin width direction inside means that the number disposed more inside than ½ of the width of the solid gather BS is larger than the number disposed more outside than this. Preferably, it is preferable to dispose the elastic stretchable member 14 only on an inner side than ½ of the width direction range in the skin contact surface of the solid gather BS. Thus, the napkin width direction in which the width direction outside of the solid gather BS curves inwardly by the contraction force of the elastic stretchable member 14 can be suppressed from deforming.

Now, it is preferable to reduce the napkin back side portion from rising on the skin side by the contraction force due to the elastic stretchable member and to improve an absorption performance and lateral leakage prevention effect by constituting a back side of the sanitary napkin 1 also in the same manner as the front side. That is, also a length of the non-fixed zone 22 of the napkin back side is set to 10 mm or longer, preferably from 10 mm to 40 mm, and more preferably from 10 mm to 20 mm.

Further, a back side end portion of the standing zone 21 is preferably disposed at a position separated by 70 mm or longer from a back end of the sanitary napkin 1. Since a napkin back side is demanded to deform more slowly than a napkin front side corresponding to the roundness of a hip, the napkin back side is set longer than a distance between a front end of the standing zone 21 of the napkin front side and a napkin front end.

Further, also on a back side of the sanitary napkin 1, it is preferable that a contour line on a front side in the longitudinal direction is unevenly formed in a width direction range where at least the solid gather BS is formed. The contour line of the end portion in the longitudinal direction may be formed unevenly in both of the front side and back side, or may be formed unevenly in any one of these.

EXPLANATION OF REFERENCE NUMERALS

1/SANITARY NAPKIN
2/IMPERMEABLE BACK SHEET
3/PERMEABLE FRONT SHEET
4/ABSORBER
5/CREPE PAPER
7/SIDE NONWOVEN FABRIC
12 to 14/ELASTIC STRETCHABLE MEMBER
20/FIXED ZONE
21/STANDING ZONE
22/NON-FIXED ZONE

The invention claimed is:

1. An absorbent article comprising: a permeable front sheet, a back sheet, an absorber interposed between the permeable front sheet and the back sheet, and a side nonwoven fabric provided on each of both side portions on the skin side,
   wherein an internal side portion of the side nonwoven fabric is folded back into double and an elastic stretchable member is disposed inside of the double sheet, and the side nonwoven fabric is partitioned into a fixed zone, a standing zone, and a non-fixed zone continuously disposed in the longitudinal direction of the absorbent article without disposing a space therebetween,
   wherein the fixed zone is a zone in which the elastic stretchable member is not joined in a stretched state to the side nonwoven fabric at both end portions in the longitudinal direction of the absorbent article and the contraction force of the elastic stretchable member does not act, and the internal side portion of the side nonwoven fabric is joined to the absorber,
   wherein the standing zone is a zone in which the elastic stretchable member is joined in a stretched state to the side nonwoven fabric in an intermediate portion in the longitudinal direction containing at least a body fluid discharge portion, and the contraction force of the elastic stretchable member makes the internal side portion of the side nonwoven fabric rise on the skin side to form a solid gather,
   wherein the non-fixed zone is a zone disposed between the fixed zone and the standing zone and in which the elastic stretchable member is not joined in a stretched state to the side nonwoven fabric and the contraction force of the elastic stretchable member does not act, and the internal side portion of the side nonwoven fabric is not joined to the absorber, and
   wherein a front side end portion of the standing zone is disposed backward of the absorbent article than a folding line (L2) along which a front side portion of the absorbent article is folded when the absorbent article is individually packed.

2. The absorbent article according to claim 1, wherein the non-fixed zone is formed with a length of 10 mm or longer in the longitudinal direction of the absorbent article.

3. The absorbent article according to claim 1, wherein a front side end portion of the standing zone is disposed at a position distanced 60 mm or larger from a front end of the absorbent article.

4. The absorbent article according to claim 1, wherein in a width direction range of at least the solid gather, a contour line of the absorbent articles corresponding to an end portion of the side nonwoven fabric in the longitudinal direction is unevenly formed.

5. The absorbent article according to claim 1, wherein the elastic stretchable member is distributed in such a manner that the number disposed more inside than ½ of the width of the solid gather is larger than the number disposed more outside than ½ of the width.

* * * * *